United States Patent
Nyte

(10) Patent No.: US 9,186,247 B2
(45) Date of Patent: Nov. 17, 2015

(54) METHOD AND SYSTEM FOR TREATMENT OF INTERNAL NASAL VALVES

(75) Inventor: Christopher Philip Nyte, Issaquah, WA (US)

(73) Assignee: E. Antonio Mangubarr, Seattle, WA (US)

( * ) Notice: Subject to any disclaimer, the term of this patent is extended or adjusted under 35 U.S.C. 154(b) by 2178 days.

(21) Appl. No.: 11/232,688

(22) Filed: Sep. 22, 2005

(65) Prior Publication Data

US 2007/0066944 A1 Mar. 22, 2007

(51) Int. Cl.
*A61F 2/18* (2006.01)
*A61F 5/56* (2006.01)
*A61M 5/32* (2006.01)
*A61F 2/30* (2006.01)

(52) U.S. Cl.
CPC .............. *A61F 2/186* (2013.01); *A61M 5/329* (2013.01); *A61F 2002/30583* (2013.01); *A61F 2210/0085* (2013.01)

(58) Field of Classification Search
CPC .................... A61M 5/329; A61F 2002/30583; A61F 2/186; A61F 2210/0085
USPC .............. 604/272; 623/10; 606/199; 424/434
See application file for complete search history.

(56) References Cited

U.S. PATENT DOCUMENTS

| | | | | |
|---|---|---|---|---|
| 4,031,569 A * | 6/1977 | Jacob | | 623/10 |
| 4,886,493 A * | 12/1989 | Yee | | 604/516 |
| 6,106,541 A * | 8/2000 | Hurbis | | 606/199 |
| 6,899,105 B2 * | 5/2005 | Krueger et al. | | 128/897 |
| 2003/0021772 A1 * | 1/2003 | Birkmayer | | 424/94.1 |
| 2003/0161824 A1 | 8/2003 | Rackley | | |
| 2006/0257488 A1 * | 11/2006 | Hubbard | | 424/486 |
| 2006/0276817 A1 * | 12/2006 | Vassallo et al. | | 606/185 |

* cited by examiner

*Primary Examiner* — Julian W Woo
(74) *Attorney, Agent, or Firm* — Chris Whewell

(57) ABSTRACT

Internal nasal valve involves injecting a biomaterial filler into the internal nasal valve of the patient. The injected biomaterial filler in the internal nasal valve increases an internal nasal valve angle.

11 Claims, 2 Drawing Sheets

METHOD AND SYSTEM FOR TREATMENT OF INTERNAL NASAL VALVES

FIELD OF THE INVENTION

The invention relates to methods for non-surgically introducing an injectable material into the nasal valve of a patient. The invention further relates to providing a non-surgical system for treatment of nasal valve collapse.

BACKGROUND OF THE INVENTION

The internal nasal valve is the narrowest point in the nasal airway and is the controlling point that regulates inspiration flow. A large percentage of inspiratory resistance is attributable to internal nasal valve function. Collapse of one or both internal nasal valves is a common cause of nasal airway obstruction, because of its narrowness, and may lead to difficulty in respiration and snoring. Internal nasal valve collapse can be a consequence of previous surgery, trauma, aging, or primary weakness of the upper lateral cartilage and is often symptomatic and debilitating.

Methods of correcting internal nasal valve collapse are typically focused on repositioning the upper lateral cartilage or adding structural grafts to support the lateral wall of the nose. The most frequent methods used surgically correct internal nasal valve collapse and involve the use of spreader grafts placed between the upper lateral cartilage and septum. Spreader grafts function by repositioning the upper lateral cartilage in a lateralized position, and by adding width to the middle nasal vault.

Spreader grafts are designed to lateralize the upper lateral cartilage by the width of the graft, thereby increasing the cross-sectional area of the nasal valve. Commonly, septal cartilage is harvested and shaped into spreader grafts. If the septum is unavailable, conchal cartilage or Medpor may be used. The grafts are placed in a sub-mucosal pocket between the septum and the upper lateral cartilage. However, spreader graft techniques are associated with complications because the nasal mucosa may be disrupted leading to web formation and further valve stenosis. In addition, surgery may be prolonged in order to perform final trimming to remove any sharp edges that may be visible or palpable resulting in added trauma to a patient's implant area.

Other surgical rhinoplasty techniques of internal nasal valve repair include suture-suspension and flaring techniques, butterfly grafts, and alar batten grafts, as well as septoplasty, turbinoplasty, and aperture widening. Each of the techniques are invasive surgical techniques that are costly and involve a degree of morbidity. In addition, the invasive surgical techniques may require hospital stays and involve long recoveries.

Methods and systems for repairing internal nasal valves including internal nasal valve collapse are desirable that eliminate invasive surgical techniques in order to reduce morbidity, eliminate hospital stays, and shorten recovery periods.

BRIEF SUMMARY OF THE INVENTION

Objects of the present invention include providing a method and system for treating internal nasal valve collapse. According to the present invention, this is achieved by non-surgical treatment. Treatment of the internal nasal valve includes injecting a biomaterial filler into the internal nasal valve of the patient. The injected biomaterial filler in the internal nasal valve, according to the invention, causes an increase in an internal nasal valve angle.

In certain embodiments, the increase in internal nasal valve angle is effected by the biomaterial filler displacing the upper lateral cartilage portion laterally away from the septal cartilage portion of the internal nasal valve.

In another embodiment, the biomaterial filler is injected into a junction of an upper lateral cartilage portion and a septum cartilage portion of the internal nasal valve. The biomaterial filler may be a gel cartilage matrix, for example.

In another embodiment, the treatment method includes inserting an injection device to an end point of the internal nasal valve and injecting the biomaterial filler at the end point and along an injection device withdrawing path up to a point of injection external to the patient.

In one embodiment, treatment includes injecting at least one 0.05 ml aliquot of biomaterial filler. Alternatively, a plurality of 0.05 ml aliquots of biomaterial filler at a plurality of positions of the internal nasal valve In one embodiment, the treatment method may include increasing a patient's internal nasal valve angle so that the treatment results in a 10-15 degree internal nasal valve angle.

The treatment method, according to embodiments of the invention, may be used to treat, nasal snoring, sleep apnea, and/or internal nasal valve collapse.

In another embodiment, a system for non-surgically treating an internal nasal valve of a patient includes a control syringe; and a 2-inch, 25 gauge thin-thin wall short bevel needle. The needle including a 10-20 degree bend at the terminal portion of the needle about 0.25 inches from the terminal end; and a hub for fluidly coupling to the control syringe.

In another embodiment, the control syringe is a 1.0 cc control syringe. Alternatively, the control syringe is a 0.3 cc control syringe.

The needle, according to an embodiment of the invention includes a 15 degree bend at the terminal portion of the needle about 0.25 inches from the terminal end. According to a further embodiment, the needle may include a straight needle fluidly coupled to a hub, the straight needle capable of fluidly coupling to the 2-inch needle, and the hub capable of fluidly coupling to the control syringe. According to certain embodiments of the invention, the needle may be stainless steel or polypropylene.

In another embodiment the system for treating internal nasal valves includes a pre-loaded syringe with a biomaterial filler. In one embodiment, the biomaterial filler is a gel cartilage matrix. In another embodiment, the biomaterial filler is a calcium hydroxylapatite gel.

BRIEF DESCRIPTION OF THE DRAWINGS

The invention will now be described by way of describing exemplary embodiments, including preferred embodiments, with reference to the accompanying Figures.

DETAILED DESCRIPTION OF THE INVENTION

Methods and systems for non-surgically treating a patient's internal nasal valve are disclosed. The internal nasal valve is made up of the junction of the upper lateral cartilage and dorsal septum which forms an angle typically considered normal in the range of 9-15 degrees. An internal nasal valve angle of approximately 10 degrees or less may be a factor contributing to nasal snoring or sleep apnea in a patient. Sleep apnea is occurs when a person stops breathing during sleep. Apnea is common among people who snore and/or in people who have anatomical abnormalities such as internal nasal valve collapse due to increased nasal resistance. Treating a patient's internal nasal valve non-surgically involves injecting a material along a patient's internal nasal valve in order to reverse collapse of the patient's internal nasal valve. The treatment thereby allowing opening of one or both nasal passages of a patient and/or reducing or eliminating snoring in a patient.

Methods and systems of the present invention include the use of biomaterial fillers in the nose as an effective injectable spreader graft to treat internal nose valve collapse. Biomaterial fillers may include a gel cartilage matrix or calcium hydroxylapatite (CaHA) filler material. CaHA material includes Radiesse manufactured by Bioform, Inc., which is a sterile, latex-free, cohesive material composed of CaHA microspheres having similar constituents as bone and teeth. Biomaterial used in embodiments of the present invention are injectable through a needle.

According to one embodiment, CaHA gel may be injected into a bilateral internal nose valve-collapsed patient's sub-mucoperichondrial plane at the junction of the patient's upper lateral cartilage and septum. In another embodiment, a gel cartilage matrix may be injected into one or both sides of an internal nasal valve collapsed patient's sub-mucosal plane at the junction of the patient's upper lateral cartilage and septum, and at locations posterior to the junction as needed.

Figure 1:
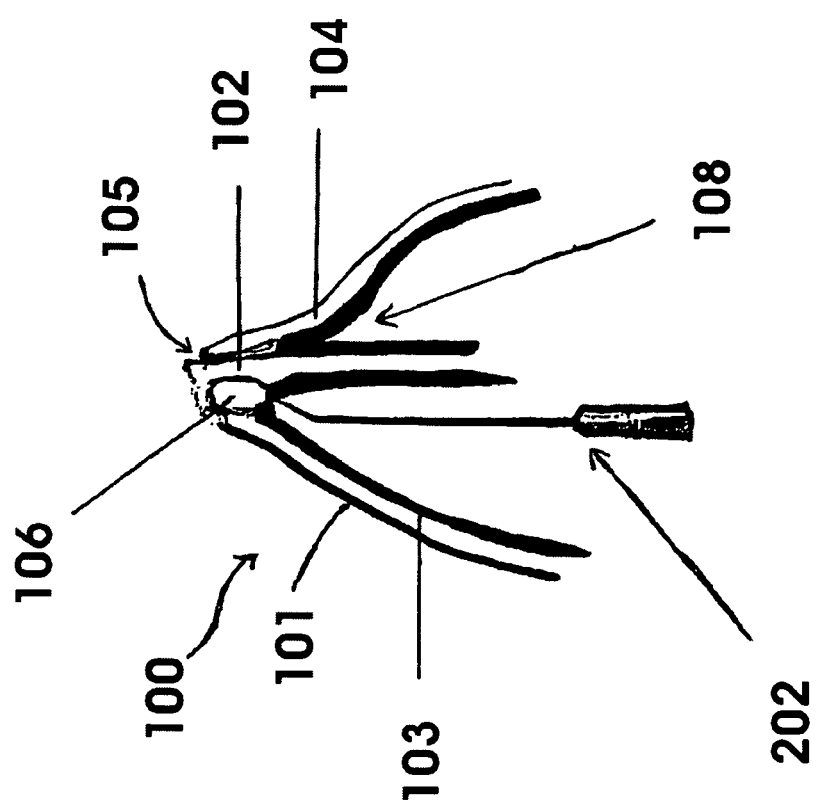
FIG. 1 depicts a cross-sectional view of the internal nasal valve portion of the nose in which embodiments of the present invention may be performed.

FIG. 1 depicts a cross-sectional view of the internal nasal valve portion of the nose 100 in which embodiments of the present invention may be performed. Cross-sectional view of nose 100 includes skin 101, septum cartilage 102, mucosa 103, upper lateral cartilage 104, and an internal nasal valve apex 105. According to an embodiment of the invention, gel cartilage matrix is injected at the apex 105 of the internal nasal valve and at points just under it (posterior) using spreader graft injection needle 202. Injection of the gel cartilage matrix at the apex 105 moves upper lateral cartilage 104 laterally away from septum cartilage 102. The amount of gel cartilage matrix injected into nose 101 is determined by the collapsed internal nasal valve angle before treatment and the desired internal nasal valve angle. Treatment of nasal valve collapse may further include injecting biomaterial back to the nasal bone (not shown).

The right side of nose 100 in FIG. 1 depicts a cross-sectional pre-treatment view, and the left side of nose 100 depicts a post-treatment view using a treatment method according to an embodiment of the invention. On the right side of nose 100 the upper lateral cartilage 104 is seen curving inward toward the nasal septum 102. The arrow on the right side of nose 100 indicates the apex 105 of the right side of the patient's nose where injection of biomaterial filler may take place, using a methods according to embodiments of the invention. For example, apex 105 may correspond with the junction between the septum and the upper lateral cartilage. The left side of nose 100 is shown with injected biomaterial filler serving as an injected spreader graft 106. The biomaterial filler serving as an injected spreader graft 106 moves upper lateral cartilage 104 laterally away from septum 102 resulting in a an increased internal nasal valve angle and a stiffening of upper lateral cartilage 202. In some embodiments, the post-treatment internal nasal valve angle is 10-15 degrees. However, small increases in internal nasal valve angle will decrease nasal valve resistance, and in some cases dramatically.

In another embodiment of the present invention, biomaterial filler, such as CaHA gel, is injected in small aliquots, e.g., 0.05 ml aliquots, at points along the upper lateral cartilage and septum junction in order to produce a stiff scaffolding effect similar to surgically placed septal or conchal cartilage grafting. The injections may be performed three times along the junction between the dorsal septum and upper lateral cartilage, for example. After each of the three 0.05 cc CaHA injections, which may be performed on one or both sides of the internal nasal valve, the upper lateral cartilage may move laterally away from the nasal septum and become less flaccid, resulting in a wider valve angle and an improvement in airflow corresponding to the increased internal nose valve angle.

In another embodiment of the present invention, the end point for CaHA injection into an internal nasal valve is upon the cantilever effect of the CAHA graft resulting in the stiffening of the upper lateral cartilage sufficient to produce minimal collapse of the internal nasal valve during inspiration with manual contralateral nostril occlusion.

Internal nasal valve collapse treatment procedures may be performed under local or topical anesthetic in a non-surgical setting. For example, a topical anesthetic on a cotton ball may be applied to a patient's nose for 10 minutes before injection of the biomaterial filler. This allows local or topical anesthetics to be titrated to effect applying or injecting only what is needed for symptomatic relief of nasal obstruction.

In another embodiment of the present invention, a system for treating internal nasal valve collapse involves providing CaHA in a single, sterile, pre-filled, 0.3-cc syringe. Alternatively, the system may include a 1.0-cc syringe. Such syringes may be obtained through Bioform Inc. A speculum may be used in order to displace the ala and superior medial aspect of the upper lateral cartilage away from the dorsal septum. Once the junction is exposed, CaHA may be injected with a 25 gauge needle. For example the injection may include introducing three 0.05 ml aliquots (totaling 0.15 cc) into the sub-mucoperichondrial plane at the junction between the dorsal septum and upper lateral cartilage. Alternatively, small aliquots of biomaterial filler may be injected into the sub-mucosal plane. The injection device used for the injection of biomaterial filler, according to embodiments of the invention, may include any type of control syringe capable of holding biomaterial filler, and may include any type of needle suitable for introducing biomaterial filler into the internal nasal valve of the nose, such as a 23 gauge 1.5" needle, in order to increase the internal nasal valve angle.

Figure 2:
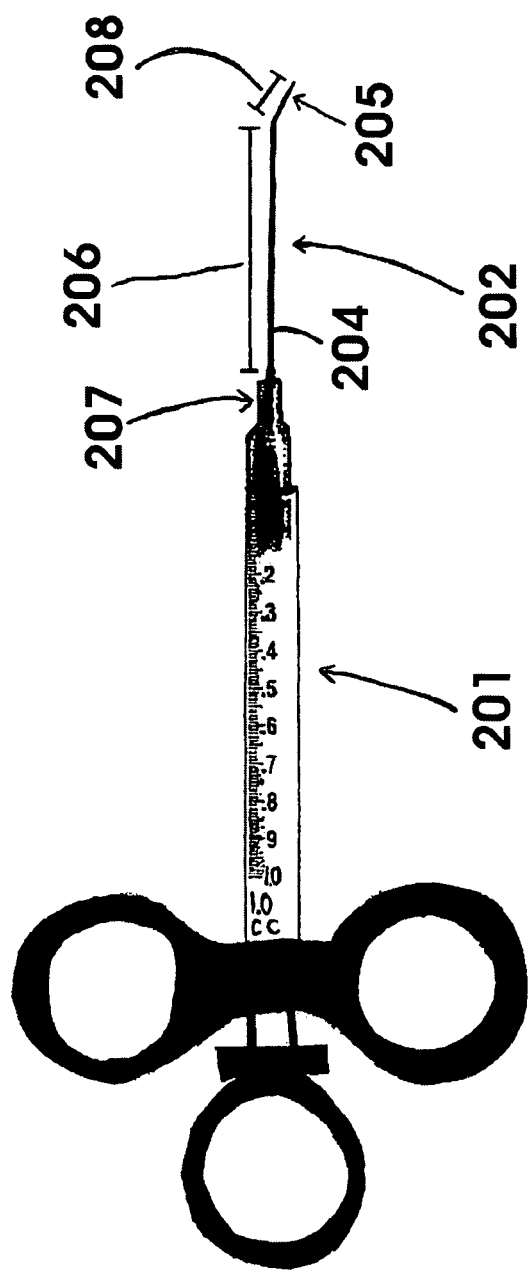
FIG. 2 depicts an intranasal injection system for treating internal nasal valve collapse in accordance with an embodiment of the invention.

In yet another embodiment of the present invention, and in accordance with FIG. 2, an intranasal injection system 200 for treating internal nasal valve collapse in accordance with an embodiment of the invention is depicted. The system 200 includes a 1.0 cc control syringe 201, a 2-inch, 25 gauge thin wall short bevel needle having about a 15 degree upward curve at the terminal end 202 (2-inch needle). An intranasal injection system 200 may be used as a spreader graft injection system where the 1.0 cc control syringe is pre-loaded with biomaterial filler, such as CaHA, and the 2-inch needle 202 being configured for injecting into the junction between the upper lateral cartilage and the septum. The 2-inch needle may be, 25 gauge thin wall 204 needle having a short bevel 205. The thin wall needle may include an inner diameter of 0.012", and an outer diameter of 0.020". A 1.75 inch portion 206 of the needle extends straight from a needle hub 207. Hub 207 may be metal or polypropylene. At the end of the 1.75 inch portion 206 nearest the short bevel point 205, the needle is curved or bent at about a 15 degree angle such that the 0.25 inch terminal portion 208 of the needle points at about a 15 degree angle with respect to the 1.75 inch portion. The terminal end of the needle includes the short bevel facing upwards, such that when the 1.75 inch portion of the needle is horizontal, the 15 degree angle 0.25 inch portion of the needle is pointed upward, and the bevel facing inward. The slight curve to the needle enables easier access to internal valve over different points of the upper lateral cartilage-septal junction of the nose. The curve may provide for precise localization of the apex and points posterior at the junction of the upper lateral cartilage and septum. In addition to the 2 inch curved needle, a straight needle having a hub (not shown) may be inserted into the hub of the 2-inch needle thereby providing fluid coupling between the two needles. The hub of the second needle may also be fluidly coupled to the injection device, such as 1 cc control syringe 201. The straight needle may include a metal or polypropylene hub.

Methods using the system depicted in FIG. 2 include, for example, advancing the 2-inch needle 202 toward the osseocartilaginous junction from the apex and injecting CaHA while withdrawing the needle making the upper lateral cartilage more rigid at the septal junction. The final injection placed at the apex of the internal nasal valve, results in the upper lateral cartilage being displaced laterally away from the septum, causing a widening of the valve angle, and improving patency. In another embodiment of the invention, a series of two 0.05 cc CaHA aliquots may be injected to provide internal nasal valve patency. Compared to surgical placement of spreader grafts that extend from the osseocartilaginous junction to the internal nasal valve, some injectable spreader grafts may be shortened and injected at the apex of the internal nasal valve junction where the cantilever effect appears to be maximized, thereby improving nasal airway patency with a shorter injectable spreader graft.

Treatment of internal nasal valve collapse using the methods described above can provide long-term relief from nasal obstruction due to internal nasal valve collapse. In some instances the method may result in relief for at least 8 months. However, the example of 8 months of relief from nasal obstruction is not limiting, and treatment of internal nasal valve collapse may be effective for more than 8 months.

Methods and systems described above may result in significantly buttressing the upper lateral cartilage and stabilize valve patency. This is because biomaterial filler such as CaHA injected into the internal nasal valve acts as a buttress and stiffens the valve, thereby preventing collapse with inspiration, especially in people with inherently weak cartilages.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A method for treating an internal nasal valve of a patient comprising, injecting a biomaterial filler from a syringe and through a needle into the internal nasal valve of the patient, said biomaterial filler being present in a flowable state sufficient to enable its passage from said syringe, through said needle and into said internal nasal valve, wherein the injected biomaterial filler in the internal nasal valve increases an internal nasal valve angle.

2. The method of claim 1, wherein the increase in internal nasal valve angle results in a 10-15 degree internal nasal valve angle.

3. The method of claim 1, wherein the biomaterial filler is injected into a junction of an upper lateral cartilage portion and a septum cartilage portion of the internal nasal valve.

4. The method of claim 3, wherein the increase in internal nasal valve angle is effected by the biomaterial filler displacing the upper lateral cartilage portion laterally away from the septal cartilage portion of the internal nasal valve.

5. The method of claim 1, wherein injecting biomaterial filler is for treatment of internal nasal valve collapse.

6. The method of claim 1, wherein injecting biomaterial filler is for treatment of sleep apnea.

7. The method of claim 1, wherein injecting biomaterial filler is for treatment of nasal snoring.

8. The method of claim 1, wherein injecting comprises injecting at least one 0.05 ml aliquot of biomaterial filler.

9. The method of claim 1, wherein injecting comprises injecting a plurality of 0.05 ml aliquots of biomaterial filler at a plurality of positions of the internal nasal valve.

10. The method of claim 1, wherein injecting comprises inserting an injection device to an end point of the internal nasal valve and injecting the biomaterial filler at the end point and along an injection device withdrawing path.

11. The method of claim 1, wherein the biomaterial filler is a gel cartilage matrix.

\* \* \* \* \*